(12) United States Patent
Martini et al.

(10) Patent No.: US 7,923,027 B2
(45) Date of Patent: Apr. 12, 2011

(54) PROCESS

(75) Inventors: Luigi Martini, Harlow (GB); Philip Smith, Collegeville, PA (US); Chi Leung Li, Harlow (GB); Ronald Raby, King of Prussia, PA (US)

(73) Assignees: SmithKline Beecham Limited, Brentford, Middlesex (GB); GlaxoSmithKline LLC, Philadelphia, PA (US)

( * ) Notice: Subject to any disclaimer, the term of this patent is extended or adjusted under 35 U.S.C. 154(b) by 1017 days.

(21) Appl. No.: 10/416,116

(22) PCT Filed: Nov. 2, 2001

(86) PCT No.: PCT/EP01/12729
§ 371 (c)(1),
(2), (4) Date: Nov. 6, 2003

(87) PCT Pub. No.: WO02/38131
PCT Pub. Date: May 16, 2002

(65) Prior Publication Data
US 2004/0062806 A1 Apr. 1, 2004

(30) Foreign Application Priority Data
Nov. 8, 2000 (GB) .................................. 0027471.2

(51) Int. Cl.
*A61K 9/24* (2006.01)

(52) U.S. Cl. ...................................... 424/473; 427/2.14

(58) Field of Classification Search .................. 424/473
See application file for complete search history.

(56) References Cited

U.S. PATENT DOCUMENTS

| | | | | |
|---|---|---|---|---|
| 4,693,886 A | | 9/1987 | Ayer | |
| 4,828,273 A | * | 5/1989 | Schadler | 277/585 |
| 5,004,614 A | * | 4/1991 | Staniforth | 424/466 |
| 5,123,903 A | * | 6/1992 | Quaid et al. | 604/22 |
| 5,674,235 A | * | 10/1997 | Parisi | 606/169 |
| 2002/0136744 A1 | * | 9/2002 | McGlynn et al. | 424/400 |

FOREIGN PATENT DOCUMENTS

| | | |
|---|---|---|
| JP | 02/124251 | 5/1990 |
| JP | 10/24491 | 1/1998 |
| WO | 01/32149 | 5/2001 |

OTHER PUBLICATIONS

Rawson (Ultrasound in Food Cutting, Pevy and Mason, p. 255-269 (1997)).*
Rawson, *Ultrasound in Food Cutting*, Povey and Mason, 14 pp. 255-269 (1997).
"Ultrasonic Technology in Today's Industry," Physics Bulletin, 38 pp. 255-257 (1987).

* cited by examiner

*Primary Examiner* — Jake M. Vu
(74) *Attorney, Agent, or Firm* — Dara L. Dinner; Theodore Furman

(57) ABSTRACT

The present invention relates to a process using ultrasonic cutting for the preparation of an oral delivery device comprising a core which includes a pharmaceutically active agent covered by an outer coating which includes one or more openings communicating from the exterior of the device toward the core.

4 Claims, 2 Drawing Sheets

PROCESS

The present invention relates to a novel process for the preparation of an oral delivery device for a pharmaceutically active agent. In particular, the invention relates to a process for the preparation of an oral delivery device comprising a core which contains the active agent, having a coating with one or more openings leading toward such a core.

There is a requirement in the art to prepare oral delivery devices comprising a core which contains a pharmaceutically active agent, and having a coating with one or more openings leading to such a core. In particular, there is requirement to prepare such devices that can be used to deliver a drug substance, at a controlled rate of release, to an environment of use. Some of the devices utilised for this purpose are discussed in U.S. Pat. No. 5,004,614, which particularly relates to a controlled release device with an impermeable coating having an orifice for release of drug when the device has been orally administered and is immersed in an aqueous medium such as gastro-intestinal fluid. The impermeable coating of such a device may be applied to a tablet core according to standard pharmaceutical formulations (e.g. dip coating, compression coating etc.) and the orifice formed by removing sections of the formed coating by laser or mechanical drilling.

It has now been found that one or more openings of various size and shape may be formed in an oral delivery device more rapidly and accurately than that provided by known drilling techniques. Thus, it is an object of this invention to provide an alternative process for the preparation of oral delivery devices having a coating with one or more openings leading to a tablet core. It is a particular object of this invention to provide an improved process for the manufacture of devices of the type disclosed in U.S. Pat. No. 5,004,614, the contents of which are incorporated herein by reference. It is also an object of the invention to provide novel constructions of devices of this general type. Other objects and advantages of the invention will become apparent from the following description.

The present invention therefore provides, in a first aspect, a process for the preparation of an oral delivery device comprising a core which includes a pharmaceutically active agent, the core covered by an outer coating which includes one or more openings communicating from the exterior of the device toward the core characterised in that the said one or more openings is/are formed by removal of one or more sections of said outer coating by application of vibrational energy of ultrasonic frequency to the outer coating.

A process for making a device according to this invention may, for example, form part of a larger process which comprises the steps of:

preparing the core of the device comprising a pharmaceutically active agent;
coating the core of the device with an outer coating to thereby form a coated device;
situating the coated device in a position adapted to receive a horn by means of which ultrasonic energy may be transmitted to a location adjacent to the horn;
applying the horn at one or more locations of the coated device to thereby disrupt the outer coating;
removing disrupted outer coating material to thereby provide a coated device with one or more openings in the outer coating communicating from the exterior toward the core of the device.

The core of the device may be prepared by compressing suitable ingredients for the core, e.g. powder or granulates to form a compacted mass which comprise the core of the device (also referred to herein as "tablet core"). This may be prepared using conventional tablet excipients and formulation compression methods. Thus, the core would typically comprise the active agent or agents along with excipients that impart satisfactory processing and compression characteristics such as diluents, binders and lubricants. Additional excipients that may form part of the core of the device include flavourants, colorants and release modifying agents. Typically the active agent and excipients are thoroughly mixed prior to compression into a solid core. The core of the device can be formed by, for example, wet granulation methods, dry granulation methods, direct compression or by melt extrusion. The core can be produced according to any desired pre-selected shape such as bi-convex, hemi-spherical, near hemi-spherical, round, oval, generally ellipsoidal, oblong, generally cylindrical or polyhedral, e.g. a triangular prism shape. The term "near hemispherical" is intended to be construed in the manner described in U.S. Pat. No. 5,004,614. Preferably the core is formulated into a bi-convex shape, e.g. having two domed opposite surfaces. In addition, the core could be produced in a multi-layered (e.g. bi- or tri-layered) form. The core can comprise active agents which are suitable for use in a wide range of therapies and include those listed in U.S. Pat. No. 5,004,614. The quantity of active agent present within the core is a matter to be determined based upon typical pharmaceutical considerations, e.g. known dosages for the active materials contained therein, and is not limited by the process of this invention.

The compacted mass which comprises the core is then coated with a suitable outer coating material which can be applied to the core by conventional procedures. For example, the coating may be formed by film formation from a polymer in solution or suspension by pouring or spraying onto a preformed core. Alternatively, a core may be dip coated, melt coated or coated using known injection moulding processes. The thickness of the outer coating may for example be in the range of 1-2000 microns, although a coating thickness in the range 10 to 500 microns would typically be preferred. Alternatively, as is common in the pharmaceutical industry the amount of coating can be expressed in terms of the relative weight of coating material applied to the core. Generally as a rule of thumb, for cores of a size suitable for an oral pharmaceutical tablet every 1% of coating corresponds to ca. 10 microns thickness of coat. Typically on such a basis, the weight of coating may amount to about 1-20% of the total weight of the core and outer coating.

The outer coating may comprise a water soluble coating which may for example be an aqueous film coating. Such coating materials are well known in the art. Particularly preferred examples of such materials include hydroxypropyl cellulose (HPC), hydroxypropyl methylcellulose (HPMC) and the like.

Preferably the outer coating is "impermeable", that is to say, a coating that has properties that delay, obstruct or prevent influx of environmental fluids, e.g. a gastro-intestinal fluid, during a pre-determined time. Thus, such an outer coating can block exposure of the core to such fluids and preferably is not removed by dissolution or otherwise disrupted, before a pre-determined duration has passed. For example such a coating may be preferentially dissolve or rupture at the pH of a determined part of the gastro-intestinal system such as the intestine, so release of the active agent in significant quantity does not occur until the coated device reaches that part. The term "impermeable" is also intended to include a coating material that, whilst being to some degree permeable to environmental fluids, is capable of preventing exposure of the core except through the one or more openings sufficiently long to allow a pre-determined quantity of drug to be released. It will be appreciated by those skilled in the art that where the outer coating material used does exhibit a certain degree of permeability to environmental fluids, a thicker coating may be necessary to achieve the desired degree of impermeability. The outer coating may be comprised of any acceptable material, or blends thereof, which provide or can be adapted to provide an impermeable coating. Representative examples of such materials include those listed in U.S. Pat. No. 5,004,614.

Particularly preferred examples of materials suitable for such coatings include ethylcellulose (e.g. those sold under the trade name Surelease™), polymethacrylate copolymers (e.g. those sold under the trade name Eudragit™ and Acrylease™), and polyvinyl acetate phthalate materials (e.g. as sold under the trade name Sureteric™), biodegradable materials and hydrophobic polymers in general. The process of the invention has been found suitable to provide openings in coatings comprised of such materials.

The outer coating may comprise a single layer, or for example it may be a multi-layer coating, for example discrete respective layers comprised of the above-mentioned materials. A multi-layer outer coating may comprise an adhesive layer, for example comprised of shellac or polyvinyl acetate phthalate to facilitate the sticking of a layer to another underlying or overlying layer, or to the core prior to application of an outer layer. Alternatively a multi-layer outer coating may comprise a releasing layer which is relatively non-adhering to an adjacent layer, particularly an outwardly adjacent coating, to facilitate the removal of the material of the adjacent layer when this is disrupted by the process of the invention. A multi-layer outer coating may comprise a layer which has a desirable texture or appearance, overlying an underlying layer or the core itself, with a less attractive texture or appearance. For example the core, typically being made by compression of granules, may have a rough surface, considered less attractive by some, and a layer may be used in this way. A multi-layer outer coating may for example comprise a sealing layer which protects the core prior to use, typically being soluble in gastro-intestinal fluids. Hydroxypropylmethyl cellulose ("HPMC") is a material suitable as a sealing layer and/or as a layer with an attractive smooth surface over the surface of the core.

Such layers of a multi-layer outer coating will normally be very thin, but it has been found that the process of the invention, using ultrasonic disruption of the coating material, enables extreme precision in the depth of outer coating material disrupted and removed, thereby allowing selective removal of all or part of the thickness of one or more layer.

The opening(s) in the coating of the device is/are formed by removal of one or more sections of outer coating. For the avoidance of doubt, the term "opening" is to be taken as being synonymous with orifice, hole, passageway, aperture etc.

The one or more opening may pass all the way through the coating, i.e. providing open communication from the exterior environment of the device to the core, and in such a case the outer coating is disrupted to a depth sufficient to communicate with the core of the device. In such a mode of operation of the process of the invention the horn may disrupt only the outer coating material (whether single or multi-layer) without disrupting the core, or alternatively the horn may also disrupt core material so that the opening penetrates into the core.

Alternatively a thin layer of the coating material may be left over the core at the bottom of the opening, i.e. by means of the horn disrupting only outer coating material but not entirely penetrating the outer coating. If the coating material left over the core at the bottom of the opening is not entirely impermeable the thickness of such residual material may be such that environmental fluids slowly penetrate the layer and the active material content of the core slowly leaches out, and so maybe used to control the rate of release of the active material. For example if the outer coating is a multi-layer coat, then all or part of the thickness of one or some of the layers may be left as a residue of the coating material left over the core at the bottom of the opening, for example as an adhesive layer, a releasing layer, a layer of a desirable texture or appearance, or a sealing layer as described above.

Use of the process of this invention may result in an exposed tablet core wherein some minor level of disruption of the tablet core surface has occurred. For aesthetic or any other purposes it may be desirable to apply an additional aqueous film coat around the coated device with openings formed therein as a final stage in a larger process such as that described above.

In a form of the process of the invention in which the outer coating is multi-layer, a more consistent smooth tablet core structure that is suitable for use in a controlled release formulation, may be obtained using a process according to this invention which comprises the steps of:

preparing the core of the device comprising a pharmaceutically active agent;

coating the core of the device with a layer of a water soluble coating, preferably an aqueous film coating;

coating the coated core with an impermeable outer coating to thereby form a coated device;

situating the coated device in a position adapted to receive a horn by means of which ultrasonic energy may be transmitted to a location adjacent to the horn;

applying the horn at one or more locations of the coated device to thereby disrupt the impermeable outer coating to a depth sufficient to communicate with the water soluble coating;

removing disrupted impermeable outer coating material to thereby provide a coated device with one or more openings which are closed by a temporary protective cover provided by the water soluble coating situated between the core and the exterior of the device.

Certain devices as described above appear to be novel, therefore in a further aspect the invention provides an oral delivery device comprising a core which includes a pharmaceutically active agent, the core covered by an outer coating which includes one or more openings in the outer coating communicating from the exterior of the device toward the core, with a thin layer of the coating material over the core at the bottom of the opening. In an embodiment of this device the outer coating is multi-layer comprising plural layers, and all or part of the thickness of one or some of the layers is present over the core at the bottom of the opening.

Initially, i.e. prior to administration to a patient, the one or more openings may also initially be closed by a temporary protective cover situated between the core and the exterior of the device. Such a temporary cover may be prepared from a water soluble material that readily dissolves in gastrointestinal fluids, and thereby fully exposing the core to the exterior of the device.

The number, relative position, shape and size of openings formed in the outer coating may be chosen, inter alia, to effect the desired release rate of active drug substance. The use of the process of this invention places no limitation on these parameters. Thus, the process of this invention can be used to produce one or more openings at any position on the device including any edges or faces that may be present. Suitably in the depth direction the openings may have substantially parallel sides. Any single opening can be as small as 0.2 mm across and up to as large as a face of the tablet core, e.g. 15 mm across although openings in the range 0.5 mm-6 mm across would be more typical. The openings may have any convenient shapes, but are preferably rounded e.g. circular or elliptical. The openings can be arrayed in such a way and their number, relative position, shape and size may be so as to produce a design, trademark or other symbol such as a logo or a number e.g. identifying the quantity of active material etc. It follows from this that the process of this invention can be used to create a commercial image on the surface of coated tablet dosage forms which are to be utilised for immediate or controlled release.

The opening(s) of the device are formed by disrupting and removing section(s) of outer coating by application of vibrational energy of ultrasonic frequency using an ultrasonic system. Disruption may involve the outer coating material being destroyed, e.g. pulverised to fine particles, or the outer coating material being removed substantially intact, for example when a circular opening is made the coating material may be removed as a small disc. The coating material may be removed in any disrupted form between these extremes.

The basic elements of an ultrasonic system and known uses thereof are described by Rawson F. F. in "An introduction to ultrasonic food cutting" (Ultrasound in Food Processing, Povey M. J. W and Mason T. J. (eds), Chapter 14, Thompson science, 1997, London, pages 255-269) and "Ultrasonic Technology in Today's Industry" (Physics Bulletin, Vol. 38, 1987, pages 255-257), the contents of these references are incorporated herein by reference. A key component of such a system is the shaped horn which is attached through a shaft to an ultrasonic source and which determines the vibrational amplitude of the tip which is in contact with the material being acted upon. The ultrasonic horn utilises a half wavelength resonance section at for example 10-100 KHz, preferably 10-60 KHz; more preferably 18-55 KHz, optimally around 40 KHz, with variable amplitude, and it should be mounted in a solid frame so that vertical movement is possible upwards and downwards. Construction of such horns and associated power and control equipment is well understood in the art, and suitable equipment is commercially available, e.g. via. Rainbow Engineering Services, Letchworth, GB.

Suitably to form the opening the horn may have a tip which is applied to the core and which is in the form of a sharp edge defining the perimeter of the opening. For example, to form a round opening such an edge may be of ring or annular shape.

Ultrasonic energy may be transmitted to the tip of the horn either before or after it is brought into contact with the outer coating. Preferably, the ultrasonic energy is switched on prior to the contact being made with the outer coating.

The cutting action is provided by a combination of the pressure applied to the sharp edge cutting surface and the mechanical longitudinal vibration of the tip. The amplitude of longitudinal vibration is of particular importance and typically will be in the range 50-100 microns peak to peak. The operating power is set in order to maintain the requisite amplitude. It will be appreciated by those skilled in the art of ultrasonic cutting that a different working tip amplitude might be required to cut through an outer coating material when compared to that required to cut through an outer coating material plus tablet core material. Ultrasonic cutting devices that are known in the art can be readily programmed to provide the requisite working amplitudes. It follows from this that it is a matter of routine experimentation to determine the optimum amplitude necessary to disrupt the outer coating to a depth sufficient to communicate with the core of the device or any other desired depth as outlined above.

The coated device is situated in a position adapted to the application of a horn of an ultrasonic system to the coating, and the device and horn are relatively moved to apply the horn to the device. For the avoidance of doubt, this is intended to mean either that the coated device is moved relative to the ultrasonic system or alternatively, that the ultrasonic system is moved relative to the coated device. The latter arrangement may be employed, for instance, using a single device with a hand held ultrasonic system. Preferably, the coated device is moved-relative to the ultrasonic system by any conventional or non-conventional means. Suitable examples may include manual incursion and removal although an automated system would typically be employed.

For example one, or preferably plural coated devices may be retained in a holder, e.g. a dimple of corresponding shape in a plate, and the horn may be applied downwardly to the device. The plate may be moved by a suitable X-Y translation engine to move successive coated devices into a position suitable for the horn to be applied to each of the successive devices.

The coated devices may be rotated, inverted or otherwise manoeuvred to allow for the production of openings on all sides of the coated device. It would be appreciated that openings in the outer coating of more than one device could be made concurrently using, for example, a plurality of coated devices situated in a X-Y table and a plurality of horns operating in co-operation.

Preferably, the horn is also fitted with means to remove any disrupted outer coating material as the opening communicating from the exterior toward the core of the device is made, and such means may be a vacuum line. For example, in the case of the above mentioned ring-shaped edge the vacuum line may communicate with the interior of the ring. For example the horn may comprise a tubular part with the ring-shaped edge being at the open end of the tube, and the bore of the tube may be connected to the vacuum line. A preferred form of the ring shaped edge is provided by an end of the tubular part which is externally cylindrical, with the end of the bore immediately adjacent to the open end tapering conically internally to narrow away from the open end. A suitable angle of taper is ca. 5-10°, e.g. ca. 7°. Conveniently such a tubular part may have a side conduit leading from the bore to the outer surface of the tubular part, and the bore may be connected to the vacuum line via this side conduit. The connection may be achieved by means of a sleeve with an internal bore fitting around the tubular part and having a conduit passing through the wall of the sleeve to the exterior of the sleeve, and being connectable to the vacuum line. Suitably, seals such as elastomer washers may be provided between the outer surface of the tubular part and the inner surface of the bore of the sleeve.

Such a construction facilitates the connection of the tubular part to the vacuum line whilst applying ultrasonic energy to the horn. This construction of horn is believed to be novel.

It has been found, using the process of this invention, that one or more openings of varying size and shape may be rapidly and accurately formed in an oral delivery device. The primary advantage of the process of this invention over known laser drilling techniques is their relative speeds. This is particularly the case when a large opening (e.g. greater than 2 mm across) is required in the outer coating. It has been found that an opening of such a magnitude can be formed using the process of this invention in less than 0.2 seconds. It follows from this that the process of this invention is therefore suitable for the large scale manufacture of a pharmaceutical in which an output of 100,000 units per hour is often desirable. In addition, the low cutting forces employed with an ultrasonic system gives rise to a lower level of disruption of tablet core. This in turn leads to a smaller product wastage (weight loss) particularly in comparison to known mechanical drilling techniques. Such a process is therefore, highly cost effective with relatively low running costs.

The invention will now be described by way of example only with reference to the accompanying drawings in which.

Figure 1:
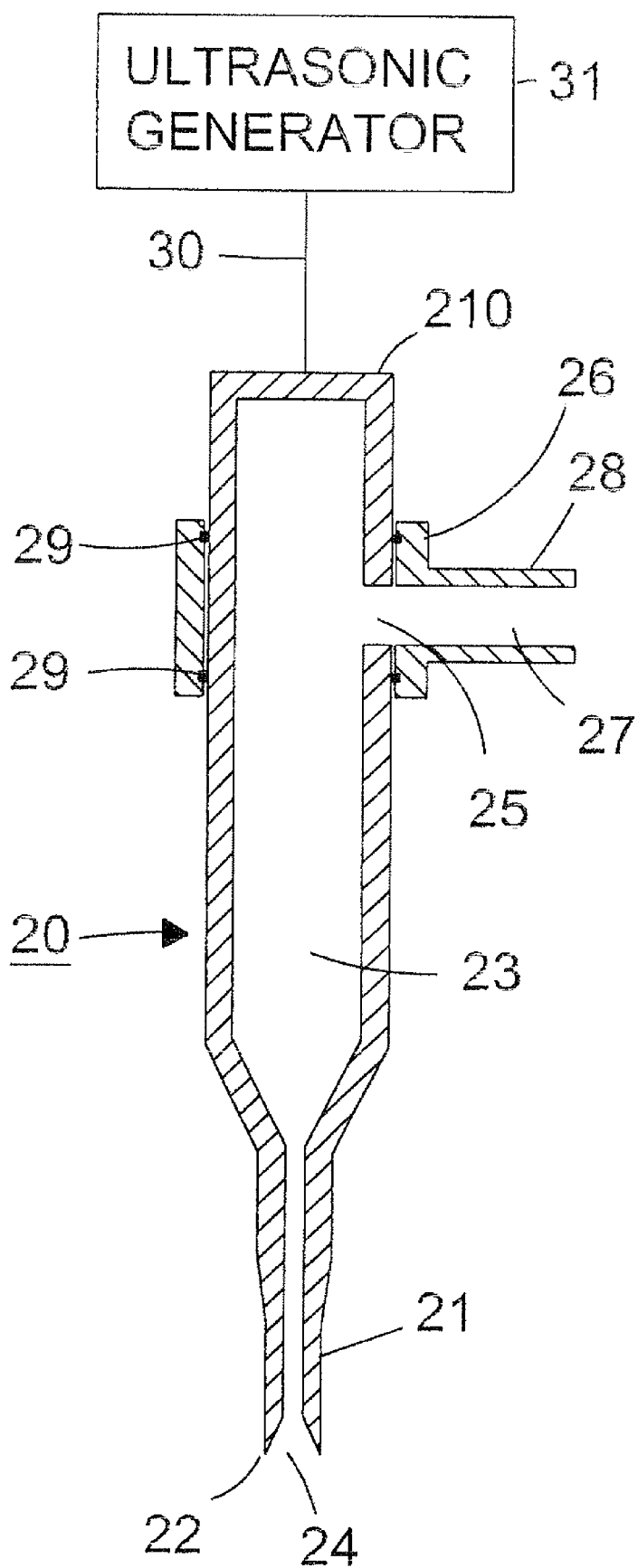
FIG. 1 shows a suitable horn for making a device of this invention, in longitudinal and cross sections.

Referring to FIG. 1, the horn 20 is made of titanium, and comprises a generally cylindrical shaped tubular part narrowing to a tip 21 at a distal end. The tip 21 is ring-shaped in cross section, corresponding in shape to the cross section of the member 20, and is profiled into a sharp edge 22 (machined as sharp as possible) having parallel, i.e., cylindrical, outer sides. Longitudinally along the center of the horn 20 is a bore 23, which may be connected to a vacuum line (not shown). Adjacent its open end 24, the bore tapers conically at a conical angle of ca. 7°, this profile being found suitable for effective cutting of the opening. Further downstream from the end 24, the internal bore widens internally, and from this wider part a side conduit 25 extends laterally. Around the tubular part, adjacent the side conduit 25, is a sleeve 26, with a bore closely conforming to the outer profile of the tubular part 20, and having a bore 27, which serves as a sleeve conduit, extending through its wall and leading to a vacuum connection 28. Between sleeve 26 and tubular part 20 are elastomeric ring washer seals 29 located respectively proximally and distally from side conduit 25 and from bore 27. At its proximal end 210, opposite the tip 21, the horn 20 is connected by a standard coupling 30 to a known ultrasonic generator 31 for applying ultrasonic energy to the horn 20. The ultrasonic generator utilized was a Rainbow Ducane DEC Press System.

Figure 2:
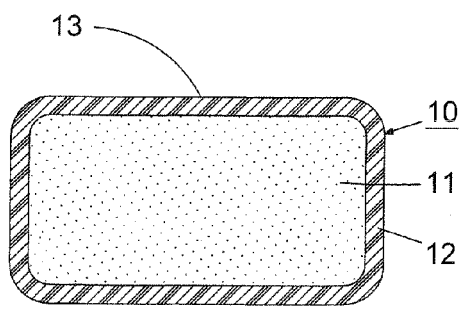
FIG. 2 shows a fully coated core comprising a pharmaceutically active drug substance and excipients.

Referring to FIG. 2, a device is shown 10 overall comprising a compressed core 11 that is suitable for use in a controlled release formulation, and which consists of 10% of a pharmaceutically active ingredient, 40% hydroxypropylmethyl cellulose (HPMC), 29% lactose, 20% microcrystalline cellulose and 1% magnesium stearate. The core 11 is made by mixing together the listed ingredients and compressing using a conventional powder compression process. The core 11 is entirely surrounded by a coating 12 which is 10% (of total weight of core and coating) of ethylcellulose, applied using a typical tablet coating process. As coated, the tablet is of a bi-convex shape having upper and lower domed sides and a circular horizontal section cut perpendicular to the plane of the drawing. The device is approximately 10 mm diameter in its circular cross section and about 4 mm thick, and the coating layer is approximately 150 microns thick.

In use the device 10 is securely supported, and the tip 21 of the horn is applied to the coating at a point 13 at the centre of one of the domed surfaces. Ultrasonic energy is then transmitted to the horn and then the tip 21 is pressed gently against the coating 12. The horn utilises a half wavelength resonance section at 18-55 KHz, preferably ca. 40 KHz, and is set to have an amplitude in the longitudinal direction of 60 microns peak to peak, maintained by the operating power of 50-100 W. Amplitude is measured as a percentage, a transducer in the system converting electrical energy to mechanical energy, to an output of 10 micron. The mechanical energy is then transferred to the booster of a particular ratio (e.g. 3:1) which increases the mechanical energy, this energy is finally transferred to the horn which again increases the mechanical energy. The amplitude is the percent of this mechanical energy and in the art is a common way of expressing the set up of the system. Such operating conditions are easily within the normal operating parameters of the system.

set by the operating power of 50-100 W. Such operating conditions are easily within the normal operating parameters of the system.

Figure 3:
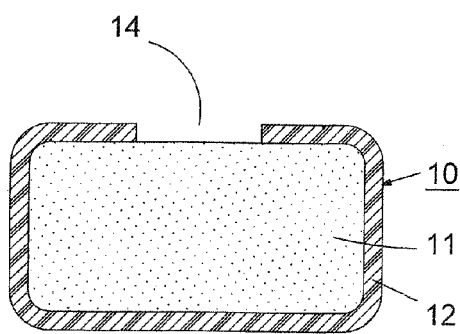
FIGS. 3, 4 and 5 show devices prepared in accordance with this invention.

Referring to FIG. 3, the tip 21 has cut an opening 14 completely through the coating 12 so that the core 11 is exposed to the outside environment of the device via the single opening. The opening 14 is substantially cylindrical in profile. During the cutting operation the particles of coating 12 material which have been removed to form the opening 14 are sucked away via the bore 23, through the side conduit 25 and out through conduit 27 of sleeve 26. It is advisable to incorporate an in-line filter between the vacuum connection 28 and the vacuum line. The diameter of the opening 14 is approximately 5.5 mm and was produced in a cutting time of less than 0.1 seconds. The weight loss of core material was found to be approximately 2%.

In further experiments, cores identical to that described above were coated with 15% of coatings being respectively a Eudragit™, a Surelease™ material and a Suretic™ material, all available from Colorcon Ltd. (GB). Circular openings of diameters 5.0, 5.5 and 6.0 mm, with depths cut accurately to predetermined distances ranging from 0.25-0.6 mm, were cut in the manner described above, using the same system at energy levels ranging from 2.8-10.0 J, peak power ranging from 50-105 W, and operating amplitudes (an operating setting of the system) of 70-100%. These openings took 0.06-0.15 seconds to cut. Further experiments successfully accurately cut openings 2.5 mm diameter.

Figure 4:
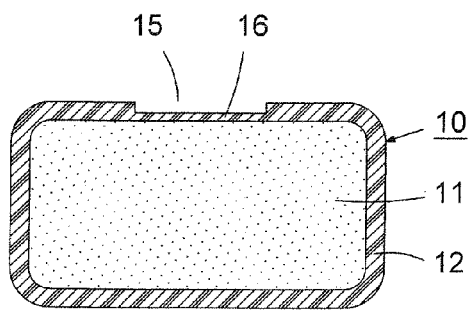
Figure 5:
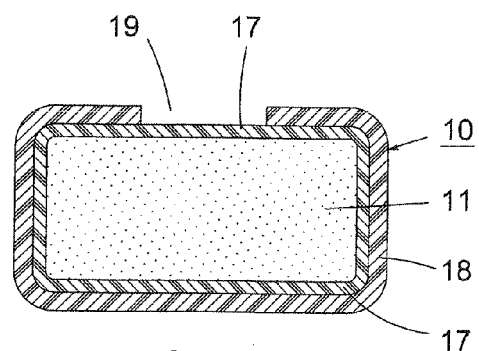

Alternative forms of the device are shown in FIGS. 4 and 5.

Referring to FIG. 4, the tip 21 has cut an opening 15 partly through the coating 12 so that the core 11 is covered by a thin layer 16 of the coating material 12 at the bottom of the opening 15, so that the core is protected from the outside environment of the device via the layer 16. The opening 15 is again substantially cylindrical in profile. It is found that such accuracy of depth cutting can be achieved with the above mentioned system.

Referring to FIG. 5, a device 10 with an outer coating which is multi-layer is shown. The outer coating layer comprises an inner layer 17 of HPMC, and an outer layer 18 of Eudragit™ material. The amount of each of the layer 17, 18 materials was ca. 10% each. The tip 21 has cut an opening 19 completely through the outer layer 18, but not through the inner layer 17, which remains wholly or partly intact at the bottom of the opening 19, so that the core 11 remains covered by layer 17 at the bottom of the opening 19. The core 11 is made from granulated materials so that it has a rough surface texture, and the HPMC layer 18 is of a smooth, attractive appearance. The inner layer 17 is exposed to the outside environment of the device via the single opening. The opening 19 is substantially cylindrical in profile. It is found that such accuracy of depth cutting can be achieved with the above-mentioned system.

It will be appreciated that the above examples are given by way of illustration rather than limitation of the utility of this invention.

The invention claimed is:

1. A process for the preparation of an oral delivery device comprising a core which includes a pharmaceutically active agent, the core covered by an outer coating which includes one or more openings extending from the exterior of the device toward the core, characterised in that the said one or more openings is/are formed by removal of one or more sections of said outer coating by application of vibrational energy of ultrasonic frequency to the outer coating, wherein the vibrational energy is applied to the outer coating by bringing into contact with the coating a sharp, ring-shaped cutting edge of the tip of an ultrasonic horn extending longitudinally toward the coating and causing the horn to vibrate longitudinally at an ultrasonic frequency, whereby the sharp ring-shaped cutting edge defines the perimeter of each said opening in the outer coating, in which said horn has proximal and distal ends and comprises a tubular part having a wall with a bore and an outer surface, and said bore has an open end at the distal end of the horn, with the sharp, ring-shaped cutting edge being at said open end, and the bore of the tubular part is connectable to a vacuum line, and wherein the step of removing one or more sections of outer coating material is carried out by drawing a vacuum through the bore of the tubular part, in which a portion of the tubular part adjacent said open end and extending therefrom is externally cylindrical, and an end portion of the bore extending from said open end has a conical taper that is narrower away from the open end than at the open end, in which said tubular part has a side conduit leading laterally through said wall from the bore of the tubular part to the exterior of the tubular part, the bore is connectable to a vacuum line via the side conduit by means of a sleeve with an internal bore having an inner surface fitting around the tubular part and being sealed thereto by elastomeric ring seals provided between the outer surface of the tubular part and the inner surface of the bore of the sleeve, said sleeve has a sleeve conduit passing through the wall of the sleeve to an outer surface of the sleeve, and the sleeve conduit is connectable at said outer surface to a vacuum line, said elastomeric ring seals are provided respectively on proximal and distal sides of the sleeve conduit and also located respectively on proximal and distal sides of the side conduit, whereby a vacuum connection is made between said vacuum line and the bore of the tubular part, and in which the step of drawing a vacuum is carried out by drawing a vacuum through said side conduit and said sleeve conduit.

2. A process for the preparation of an oral delivery device comprising a core which includes a pharmaceutically active agent, the core covered by an outer coating which includes one or more openings extending from the exterior of the device toward the core, characterised in that the said one or more openings is/are formed by removal of one or more sections of said outer coating by application of vibrational energy of ultrasonic frequency to the outer coating, wherein the vibrational energy is applied to the outer coating by bringing into contact with the coating a sharp, ring-shaped cutting edge of the tip of an ultrasonic horn extending longitudinally toward the coating, and causing the horn to vibrate longitudinally at an ultrasonic frequency, whereby the sharp ring-shaped cutting edge defines the perimeter of each said opening in the outer coating, in which said horn has proximal and distal ends and comprises a tubular part having a wall with a bore and an outer surface, and said bore has an open end at the distal end of the horn, with the sharp, ring-shaped cutting edge being at said open end, and the bore of the tubular part is connectable to a vacuum line, and wherein the step of removing one or more sections of outer coating material is carried out by drawing a vacuum through the bore of the tubular part, and in which said tubular part has a side conduit leading laterally through said wall from the bore of the tubular part to the exterior of the tubular part, the bore is connectable to a vacuum line via the side conduit by means of a sleeve with an internal bore having an inner surface fitting around the tubular part and being sealed thereto by elastomeric ring seals provided between the outer surface of the tubular part and the inner surface of the bore of the sleeve, said sleeve has a sleeve conduit passing through the wall of the sleeve to an outer surface of the sleeve, and the sleeve conduit is connectable at said outer surface to a vacuum line, said elastomeric ring seals are provided respectively on proximal and distal sides of the sleeve conduit and also located respectively on proximal and distal sides of the side conduit, whereby a vacuum connection is made between said vacuum line and the bore of the tubular part, and in which the step of drawing a vacuum is carried out by drawing a vacuum through said side conduit and said sleeve conduit.

3. A process according to claim 2, in which the horn is caused to vibrate longitudinally by application of ultrasonic energy to the proximal end of the horn by means of an ultrasonic generator.

4. A process according to claim 1, in which the horn is caused to vibrate longitudinally by application of ultrasonic energy to the proximal end of the horn by means of an ultrasonic generator.

* * * * *